United States Patent [19]

Richbourg et al.

[11] Patent Number: 4,899,468
[45] Date of Patent: Feb. 13, 1990

[54] SOLE FOR CAST SHOE

[76] Inventors: Henry L. Richbourg, 1801 Barkley Rd., Statesville, N.C. 28677; Hugh W. Dayton, 36 S. Main St., Jeffersonville, Ohio 43128

[21] Appl. No.: 823,778

[22] Filed: Jan. 29, 1986

[51] Int. Cl.⁴ .................. A43B 3/12; A61F 13/00
[52] U.S. Cl. .................................... 36/110; 36/11.5; 128/82
[58] Field of Search ............... 36/110, 11.5, 25 R, 36/33, 32 R, 83; D2/319, 322; 128/82, 83, 83.5

[56] References Cited

U.S. PATENT DOCUMENTS

| D. 252,837 | 9/1979 | Cole | D2/322 |
|---|---|---|---|
| 1,486,630 | 3/1924 | Burnett | 36/33 |
| 2,278,626 | 4/1942 | Vasko | 128/83.5 |
| 2,526,205 | 10/1950 | Doerschler | 36/11.5 |
| 3,008,469 | 11/1961 | Welch | 36/32 R |
| 3,584,402 | 6/1971 | Silverman | 36/11.5 |
| 3,802,424 | 4/1974 | Newell | 128/83.5 |
| 4,414,759 | 11/1983 | Morgan et al. | 36/11.5 |
| 4,419,836 | 12/1983 | Wong | 36/11.5 |
| 4,425,721 | 1/1984 | Spronken | 36/110 |
| 4,446,856 | 5/1984 | Jordan | 128/83.5 |

FOREIGN PATENT DOCUMENTS 1287861  9/1972  United Kingdom ............ 36/83

Primary Examiner—Steven N. Meyers
Attorney, Agent, or Firm—Sherman and Shalloway

[57] ABSTRACT

An improved sole for a cast shoe is disclosed herein, which sole includes three regions designed to combine together to form a sole enabling the user of the shoe thereof to walk with a more natural gait than is possible through the use of prior art designs. The three regions of the sole consist of an anterior portion, a weight bearing portion and a posterior portion. The posterior portion is radiused to facilitate the transition from heel strike to the stance phase of the gait. The weight bearing portion is substantially flat while the anterior portion is curved in both the anteroposterior radius and the mediolateral radius.

2 Claims, 2 Drawing Sheets

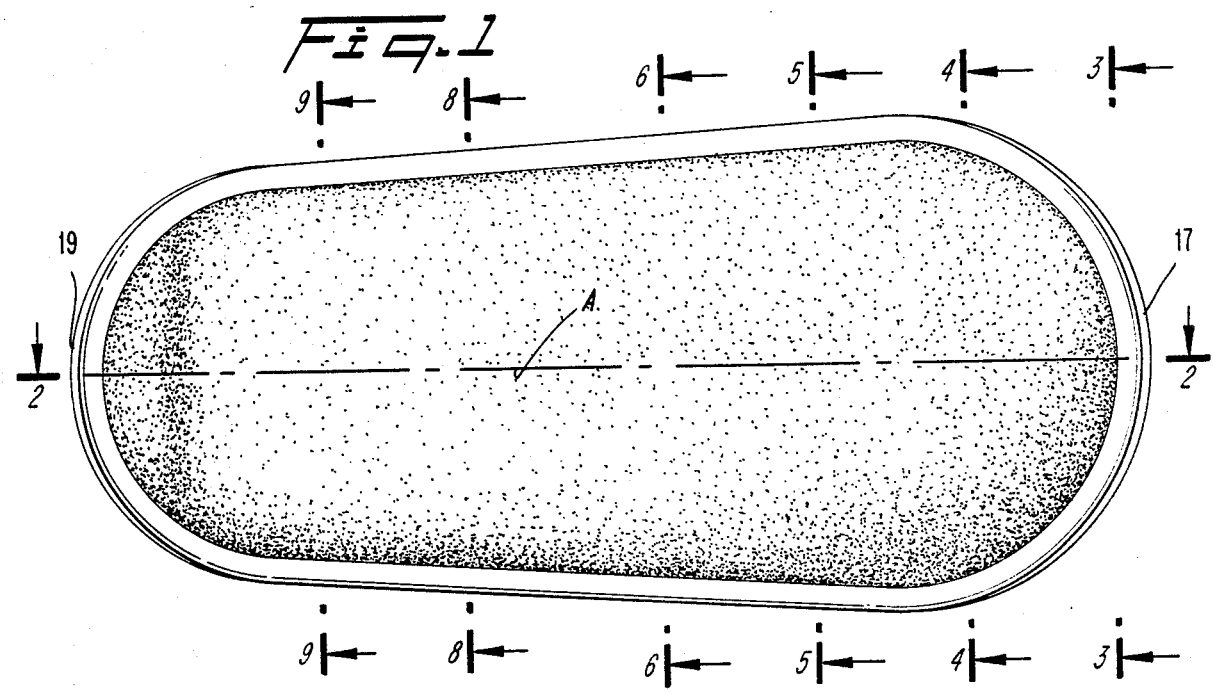
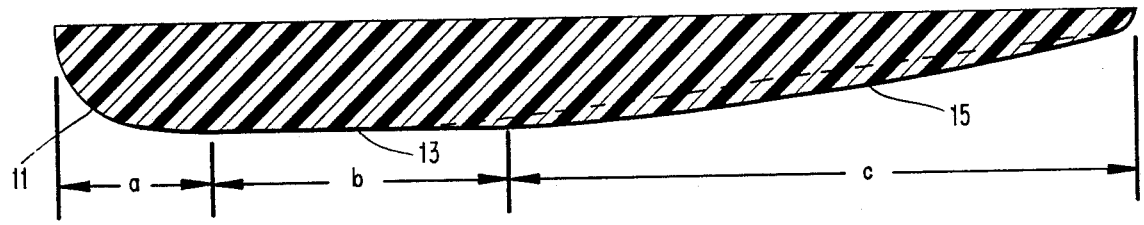
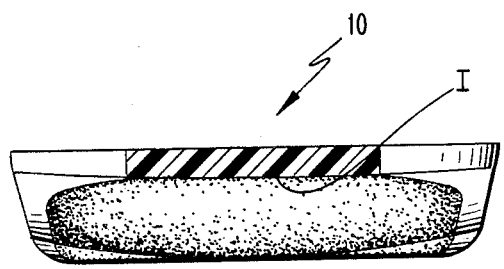 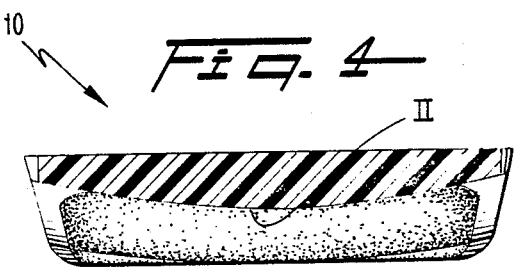

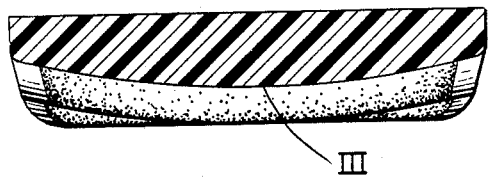
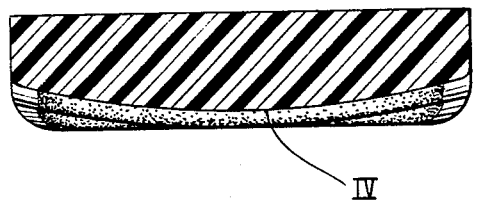
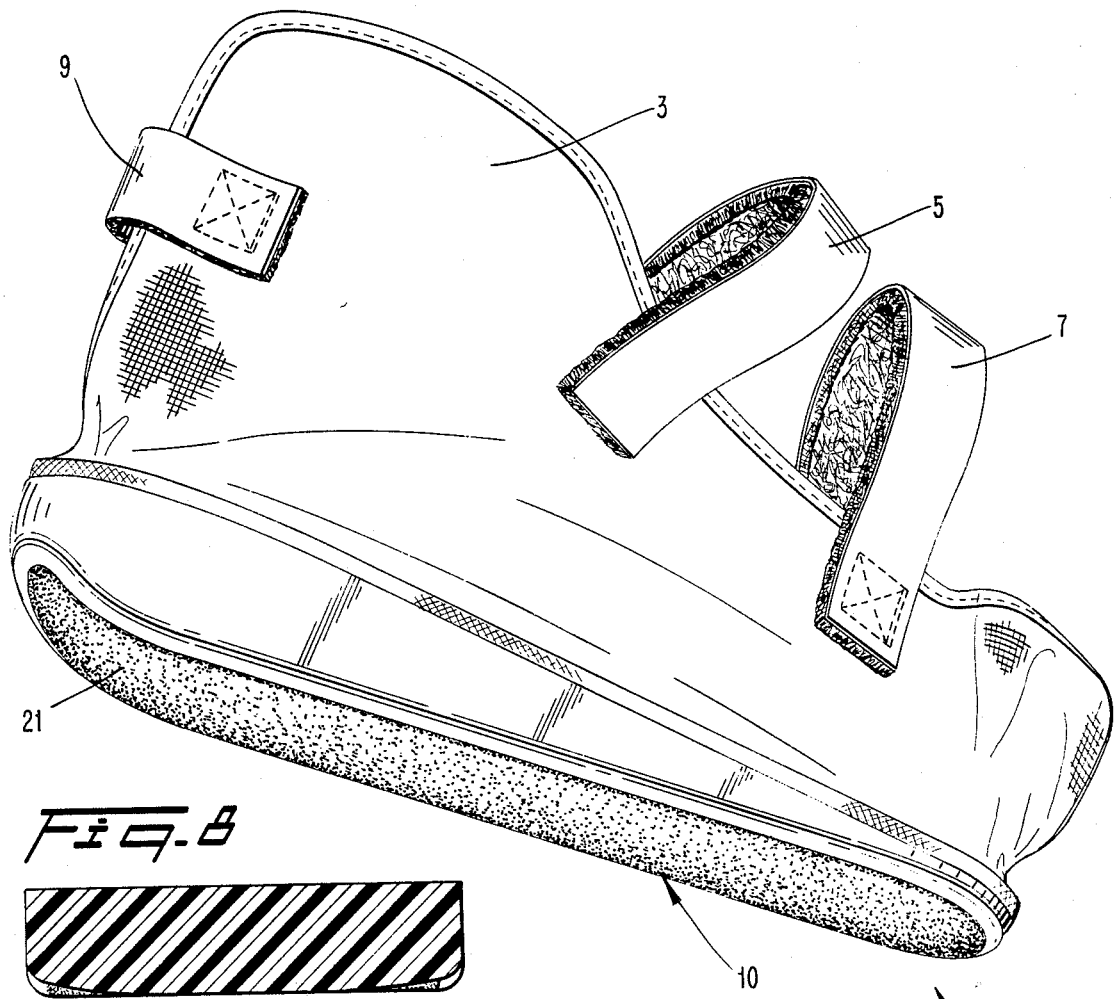
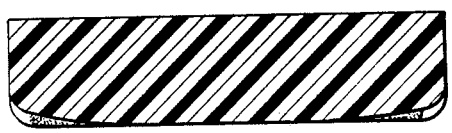

SOLE FOR CAST SHOE

BACKGROUND OF THE INVENTION

In the prior art, several examples of shoes designed to be used by a person having a walking cast are known. In these known designs, a common deficiency lies in the fact that the person using them finds it difficult to walk with a natural gait.

Some cast shoes utilize a flat bottom such as that which is disclosed in United States Patent 3,566,487. It has been found that a flat sole increases the stability of the shoe for the user but naturally results in an undesirable flat-footed gait.

As the state of the art progressed, cast shoes began to be made with a "rocker bottom" which constituted an improvement over the flat bottom designs by allowing for more of a rolling or heel-to-toe gait. Since this gait is not a natural normal gait, the rocker bottom cast shoes did not solve all of the problems which have to be solved so as to enable the users thereof to walk normally. This is because in normal walking motion, the foot rotates externally to achieve the normal "toe-off" position on the ball of the foot. This externally rotated position requires abduction of the ankle which is, of course, not possible when the ankle is rigidly immobilized in a cast. U.S. Pat. Nos. 3,584,402; 3,802,424; 4,005,704 and 4,057,056 each disclose the concept of a cast shoe having what might be termed a "rocker bottom."

Thus, a need has arisen for a cast shoe which will overcome the deficiencies attendant in prior art designs and will thus provide a cast shoe allowing the user thereof to approximate a normal gait so as to speed the rehabilitation process and aid in the patient's comfort.

SUMMARY OF THE INVENTION

The present invention overcomes the deficiencies in the prior art designs as set forth hereinabove by providing an improved sole for a cast shoe having the following combination of inventive features:

(a) In a first aspect of the present invention, the inventive sole has been designed to have three regions which consecutively merge into one another so as to combine together to form the inventive cast shoe sole.

(b) A first region consists of the posterior portion of the sole which is specially radiused to facilitate the transition from "heel strike" to the "stance phase" of the human gait. By providing a tangible surface instead of an edge for the purpose of enabling the heel to contact the ground, the posterior portion adds stability to the sole.

(c) The posterior portion merges into a second region comprising the weight bearing portion. The weight bearing portion consists of a substantially flattened area specifically designed to be located directly below the weight bearing axis of the tibia so as to provide improved stability when the user is in a standing position or in the "stance phase" of the walking gait.

(d) The weight bearing portion merges into a third region termed the "anterior portion." The anterior portion of the improved sole includes a first radius in the anteroposterior direction and a second radius in the mediolateral direction. The anteroposterior radius is made sufficiently gradual so as to provide a stable walking surface so as to enable the patient to easily make the transition from the stance phase to a "toe-off" phase. The mediolateral radius assists in approximating the normal "toe-off" position of the foot by providing a weight bearing surface under the ball of the foot. The surface of the anterior portion in the mediolateral direction is characterized by a radius which decreases in a direction from the anterior portion toward the posterior portion. This radius change is gradual and aids in defining the anteroposterior radius. The curvature of the anterior portion of the shoe in both the anteroposterior direction and the mediolateral direction is sufficiently gradual so as to maintain stability but is sufficient to guide the foot into the proper walking position.

(e) The inventive sole is made substantially symmetric about a longitudinal axis thereof so that the shoe may be used in conjunction with either the left or right foot of the patient.

Accordingly, it is a first object of the present invention to provide an improved sole for a cast shoe.

It is a further object of the present invention to provide an improved sole for a cast shoe which enables the user thereof to more closely approximate a normal walking gait.

It is a still further object of the present invention to provide an improved sole for a cast shoe, which sole is symmetrical about its longitudinal axis so that the cast shoe may be utilized in conjunction with either the left or right foot of the patient.

It is a still further object of the present invention to provide an improved sole for a cast shoe which combines improved stability on heel strike with improved stability when the patient is standing flatfooted.

It is a still further object of the present invention to provide an improved sole for a cast shoe which provides the user thereof with improved stability in the stance phase of the gait as well as in the toe-off position of the gait.

It is a still further object of the present invention to provide such an improved sole with a textured surface so as to reduce the incidence of slippage thereof to thereby improve the safety of the patient.

These and other objects, aspects and features of the present invention will be better understood from the following detailed description of the preferred embodiments when read in conjunction with the appended drawing figures.

BRIEF DESCRIPTION OF THE DRAWINGS

FIG. 1 shows a bottom view of the inventive sole.

FIG. 2 shows a cross-sectional view along the line 2—2 of FIG. 1.

FIG. 3 shows a cross-sectional view along the line 3—3 of FIG. 1.

FIG. 4 shows a cross-sectional view along the line 4—4 of FIG. 1.

FIG. 5 shows a cross-sectional view along the line 5—5 of FIG. 1.

FIG. 6 shows a cross-sectional view along the line of 6—6 of FIG. 1.

FIG. 7 shows a perspective view of the inventive sole as integrated in a cast shoe.

FIG. 8 shows a cross-sectional view along the line 8—8 of FIG. 1.

FIG. 9 shows a cross-sectional view along the line 9—9 of FIG. 1. SPECIFIC DESCRIPTION OF THE PREFERRED EMBODIMENT Reference is first made to FIG. 7 wherein a cast shoe 1 is seen to include a flexible body portion 3 adjustable straps 5, 7 and 9 and an improved sole 10 in accordance with the present invention.

As best seen with reference to FIGS. 1 and 2, the inventive sole 10 is characterized by three regions, a, b, and c. The region a defines a posterior portion of the sole 10 including a radius surface 11 provided to facilitate the transition from heel strike to the stance phase of the walking gait. As explained hereinabove, the surface 11 also improves stability on heel strike by providing a surface instead of an edge for the heel to contact the ground.

The region b defines a weight bearing portion having a substantially flat surface 13 which is specifically designed to be located in axial alignment with the weight bearing axis of the tibia of the leg of the user thereof. By locating the weight bearing portion of the sole 10 coaxial with the weight bearing axis of the tibia and by making the surface 13 substantially flat, improved stability results when the patient is in a standing position or in the stance phase of the walking gait. FIGS. 8 and 9 show how the weight bearing portion broadens as one moves along the sole in the direction from anterior to posterior.

The region c defines the anterior portion of the sole 10 and includes as best seen in FIG. 2 a curved surface 15 in the anteroposterior direction. The surface curvature 15 of the anterior portion is made gradual so as to provide a stable walking surface so as to enable the patient to better make the transition from the stance phase of the walk to the toe-off phase.

As seen with reference to FIGS. 3, 4, 5 and 6, the anterior portion of the sole is also curved in the mediolateral direction. As may be seen from a comparison of FIG. 1 on the one hand and FIGS. 3, 4, 5 and 6 on the other hand, the radius of curvature of the anterior portion of the sole 10 becomes smaller as one traverses the region c from the front surface 17 toward to region b. Thus, FIG. 3 shows a cross-sectional view of the region c where the radius of curvature of the anterior portion of the sole is at a radius defining a curvature I. In a similar fashion, FIGS. 4, 5 and 6 respectively show cross-sectional views of locations on region c where the mediolateral radius of curvature defines the respective curvatures II, III and IV. The mediolateral radius of curvature is varied in this fashion for three reasons. Firstly, it facilitates the definition of the surface 15 best seen in FIG. 2 since the decreasing radius of curvature in the anterior to posterior direction causes the sole to bow out further and further thereby defining the curvature designated by reference numeral 15 in FIG. 2. Additionally, this variance in the radius of curvature assists the patient in approximating the normal toe-off position by providing a weight bearing surface under the ball of the foot. The curvature is gradual enough to allow the patient to maintain stability but is sufficiently large so as to guide the foot into the proper walking position. Finally, the variance in the radius of curvature provides a surface which allows the lower leg to naturally rotate externally to achieve the normal "toe-off" position on the ball of the foot.

As best seen in FIG. 1, the sole 10 is symmetric about the longitudinal axis A thereof. Accordingly, this fact taken in conjunction with the fact that the sole 10 is wider at the anterior portion than it is at the posterior portion, results in the shoe 11 being usable for either the left or the right foot. Thus, the present invention is not only designed to better facilitate the normal walking but is also designed with the flexibility of being usable with either foot of the patient.

As best seen in FIG. 7, the bottom surface of the sole 10 is textured as designated by reference numeral 21 so as to reduce the incidence of slippage to thereby improve patient safety. In order to further facilitate the reduction in the incidence of slippage, it is contemplated that the inventive sole 10 be constructed from a light weight polyurethane material. This material is intended to cushion the impact loading at heel strike on the posterior portion so as to therefore reduce the incidence of cast breakage. The inherent texture of polyurethane material combines with the textured portion 21 so as to further reduce the incidence of slippage.

Of course, if desired, the sole 10 may be made of any light weight rubber or plastic which allows good traction with ground surfaces.

FIG. 2 also shows in phantom line, the projection of the edge of the sole upon the centerline thereof. Comparison of the phantom and full lines in FIG. 2 should facilitate a better understanding of the curvature of the sole in the mediolateral direction.

Thus, an improved sole for a cast shoe has been disclosed hereinabove in terms of a perffered embodiment thereof. Various changes, modifications, alterations and additions to the structure and functions disclosed hereinabove may be contemplated by those skilled in the art without departing from the spirit and scope of the present invention. Accordingly, it is intended that the present invention only be limited by the terms of the following claims.

We claim:

1. In a cast shoe, an improved sole comprising:
   (a) a posterior portion having a curved surface;
   (b) a substantially flat weightbearing portion adjacent said posterior portion; and
   (c) an anterior portion adjacent said weightbearing portion and having an anteroposterior curvature so as to provide a stable walking surface and having a mediolateral curvature so as to provide assistance in approximating a normal toe-off position during walking, wherein said mediolateral curvature varies in radius of curvature in the anterior to posterior direction.

2. The invention of Claim 1, wherein said radius of curvature decreases in said anterior to posterior direction.

* * * * *